United States Patent
Wang et al.

(10) Patent No.: US 11,133,476 B2
(45) Date of Patent: Sep. 28, 2021

(54) ELECTRON TRANSPORT MATERIAL, AN OLED DISPLAY PANEL AND AN ELECTRONIC DEVICE COMPROMISING THE SAME

(71) Applicant: SHANGHAI TIANMA AM-OLED CO., LTD., Shanghai (CN)

(72) Inventors: Miao Wang, Shanghai (CN); Xiangcheng Wang, Shanghai (CN); Ying Liu, Shanghai (CN); Yuji Hamada, Shanghai (CN); Jinghua Niu, Shanghai (CN)

(73) Assignee: SHANGHAI TIANMA AM-OLED CO., LTD., Shanghai (CN)

( * ) Notice: Subject to any disclaimer, the term of this patent is extended or adjusted under 35 U.S.C. 154(b) by 622 days.

(21) Appl. No.: 15/673,327

(22) Filed: Aug. 9, 2017

(65) Prior Publication Data

US 2017/0338422 A1    Nov. 23, 2017

(30) Foreign Application Priority Data

Feb. 15, 2017    (CN) .......................... 201710081427.2

(51) Int. Cl.
```
H01L 51/54     (2006.01)
H01L 51/00     (2006.01)
C07D 471/04    (2006.01)
C07D 519/00    (2006.01)
H01L 51/50     (2006.01)
H01L 51/52     (2006.01)
```

(52) U.S. Cl.
CPC ........ *H01L 51/0072* (2013.01); *C07D 471/04* (2013.01); *C07D 519/00* (2013.01); *H01L 51/0052* (2013.01); *H01L 51/0058* (2013.01); *H01L 51/0067* (2013.01); *H01L 51/5012* (2013.01); *H01L 51/5056* (2013.01); *H01L 51/5072* (2013.01); *H01L 51/5088* (2013.01); *H01L 51/5092* (2013.01); *H01L 51/5206* (2013.01); *H01L 51/5221* (2013.01); *H01L 2251/301* (2013.01); *H01L 2251/308* (2013.01)

(58) Field of Classification Search
CPC ............ H01L 51/0072; H01L 51/0052; H01L 51/0058; H01L 51/0067; H01L 51/0061; H01L 51/0059; H01L 51/006; H01L 51/5072; H01L 51/5076; H01L 51/5052; C07D 471/04; C07D 471/14; C07D 471/22; C07D 519/00
See application file for complete search history.

(56) References Cited

U.S. PATENT DOCUMENTS

| | | | |
|---|---|---|---|
| 2004/0076853 A1 | 4/2004 | Jarikov | |
| 2004/0080476 A1* | 4/2004 | Tsai | .................... H01L 27/3244 345/82 |
| 2004/0265626 A1* | 12/2004 | Shibanuma | .......... C07D 471/04 428/690 |
| 2009/0001327 A1* | 1/2009 | Werner | ................. H01L 51/002 252/512 |
| 2014/0048854 A1 | 2/2014 | Wang et al. | |
| 2014/0152619 A1 | 6/2014 | Hotelling et al. | |

FOREIGN PATENT DOCUMENTS

| | | |
|---|---|---|
| CN | 101121715 A | 2/2008 |
| CN | 105096879 A | 11/2015 |
| EP | 2381502 B1 | 8/2013 |
| JP | 2003017268 A | 1/2003 |

OTHER PUBLICATIONS

Enomoto et al., machine translation of JP 2003-017268 (2003) pp. 1-25. (Year: 2003).*
Xu et al., "Low-Roughness and Easily-Etched Transparent Conducting Oxides with a Stack Structure of ITO and IZO" ECS Journal of Solid State Science and Technology, vol. 2, issue 11 (2013), R245-R248. (Year: 2013).*
DE, Application 102017120733.3, 1st Office Action dated Nov. 27, 2018.

* cited by examiner

*Primary Examiner* — Dylan C Kershner
(74) *Attorney, Agent, or Firm* — Alston & Bird LLP

(57) ABSTRACT

The present disclosure relates to an electron transport material having a structure represented by formula (I). The present disclosure enhances the glass transition temperature of the material by way of increasing the molecular weight thereof through modifying phenanthroline, without influencing the electron transport property of the material. A novel type of electron transport material having a glass transition temperature of more than 100° C. is designed by the present disclosure. The compound provided by the present disclosure is used as an electron transport material, i.e. as an electron transport layer; and the compound is doped with metals for use as an electron injection layer, thereby improving the efficiency of an OLED device and reducing the operation voltage.

12 Claims, 2 Drawing Sheets

ELECTRON TRANSPORT MATERIAL, AN OLED DISPLAY PANEL AND AN ELECTRONIC DEVICE COMPROMISING THE SAME

CROSS-REFERENCE TO RELATED APPLICATIONS

This application claims priority of Chinese Patent Application No. CN201710081427.2, filed on Feb. 15, 2017, the entire contents of which are hereby incorporated by reference.

TECHNICAL FIELD

The present disclosure relates to the field of organic electroluminescent materials, and especially to an electron transport material, an OLED display panel and an electronic device comprising the same, and more particularly to the synthesis of a nitrogen-containing electron transport material and its application in an organic electroluminescent device.

BACKGROUND

Bphen (4,7-diphenyl-1,10-phenanthroline)

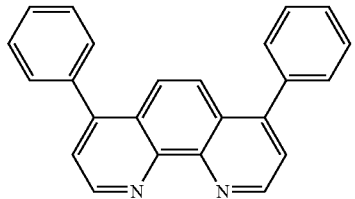 [SMILES: c1ccc(-c2ccnc3c2ccc2c(-c4ccccc4)ccnc23)cc1]

with low molecular weight has a relatively high electron mobility ($5.2 \times 10^{-4}$ cm$^2$/Vs, $5.5 \times 10^5$ V/cm) due to its rigid plane structure, and is therefore widely used as the material for an electron transport layer for an organic light emission display device.

CN101121715B discloses a phenanthroline derivative compound and a method for producing it, and its application as an electron transport material, in a light emitting element of a light emitting device. A phenanthroline derivative compound is represented by its molecular formular

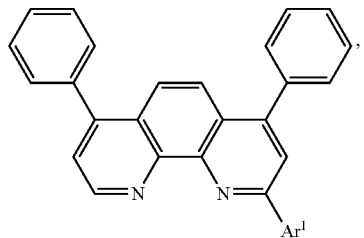

wherein Arl represents an aryl group, preferably a substituted or unsubstituted phenyl group, a substituted or unsubstituted naphthyl group, a substituted or unsubstituted anthryl group, or a substituted or unsubstituted phenanthryl group. As the preferred compounds, for example, TMPBP, NaBP, and PBPE, and the like can be listed. In the light emitting element, the light emitting device, and the electronic device, it is preferable that the compound is contained in the light emitting layer. In this case, it is preferable to use the compound as the main body.

However, the existing phenanthroline compound has a relatively too low glass transition temperature Tg of only 62° C., although it can form a non-crystalline film in the vacuum evaporation, the device is susceptible to decay when in operation, thereby affecting the stability of the device.

Therefore, a technical problem to be solved in the art is how to develop a phenanthroline-based electron transport material with a higher glass transition temperature, and how to use the electron transport material to produce an electron transport layer and an electron injection layer.

SUMMARY

In view of the deficiencies in the related technics, the first objective of the present disclosure is to provide an electron transport material having a structure represented by formula (I):

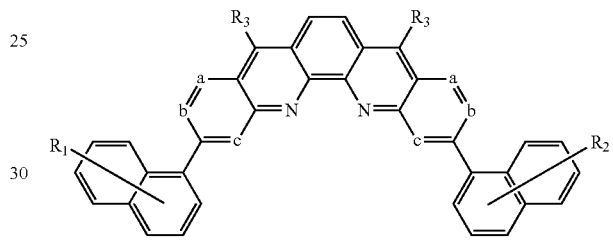

Formula (I)

in formula (I), a, b and c are each independently selected from the group consisting of $CR_4$ and N; wherein $R_4$ is any one or a combination of at least two selected from the group consisting of a hydrogen atom, a substituted or unsubstituted hydrocarbyl, a heterocyclic group, a halogen atom, a nitro group, a cyano group,

—$OR_7$, —$SR_8$ and —$COOR_9$; wherein, $R_5$, $R_6$, $R_7$, $R_8$, and $R_9$ are each independently any one or a combination of at least two selected from the group consisting of a hydrogen atom, a substituted or unsubstituted hydrocarbyl, and a heterocyclic group;
in formula (I), $R_1$, $R_2$, and $R_3$ are each independently any one or a combination of at least two selected from the group consisting of a hydrogen atom, a deuterium atom, a substituted or unsubstituted hydrocarbyl, and a heterocyclic group.

The second objective of the present disclosure is to provide an OLED display panel comprising a first electrode and a second electrode, wherein a laminate comprising a light emitting layer and an electron transport layer is disposed between the first electrode and the second electrode, and the material of the electron transport layer includes an electron transport material as described in the first object of the present disclosure.

The third objective of the present disclosure is to provide an electronic device comprising an OLED display panel as described in the second object of the present disclosure.

DETAILED DESCRIPTION

Figure 1:
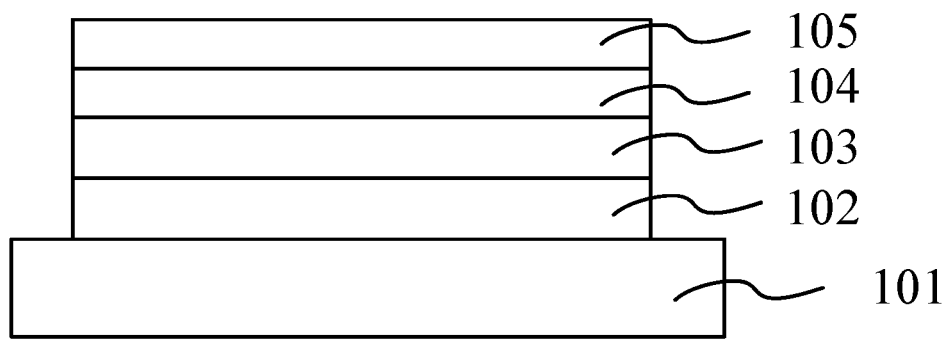
FIG. 1 is a cross-sectional structural representation of an OLED display panel provided in a specific embodiment of the present disclosure.

For the purpose of understanding the present disclosure, the following examples are listed below in the present disclosure. It will be apparent to those skilled in the art that the examples are merely illustrations of the present disclosure and should not be construed as specific limitations of the present disclosure.

In one specific embodiment, the present disclosure provides an electron transport material having a structure represented by formula (I):

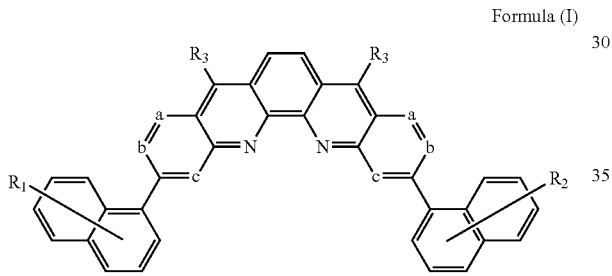

Formula (I)

in formula (I), a, b and c are each independently selected from the group consisting of $CR_4$ and N; wherein $R_4$ is any one or a combination of at least two selected from the group consisting of a hydrogen atom, a substituted or unsubstituted hydrocarbyl, a heterocyclic group, a halogen atom, a nitro group, a cyano group,

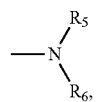

$-OR_7$, $-SR_8$ and $-COOR_9$; wherein, $R_5$, $R_6$, $R_7$, $R_8$, and $R_9$ are each independently any one or a combination of at least two selected from the group consisting of a hydrogen atom, a substituted or unsubstituted hydrocarbyl, and a heterocyclic group;

in formula (I), $R_1$, $R_2$, and $R_3$ each independently represents any one or a combination of at least two selected from the group consisting of a hydrogen atom, a deuterium atom, a substituted or unsubstituted hydrocarbyl, and a heterocyclic group. The present disclosure enhances the glass transition temperature of a material by way of increasing the molecular weight thereof through modifying the phenanthroline, meanwhile without influencing the electron transport property of the material, whereby a novel type of electron transport material having a glass transition temperature of more than 100° C. is designed by the present disclosure.

Preferably, the substituted or unsubstituted hydrocarbyl includes any one or a combination of at least two of a substituted or unsubstituted C1-C30 linear or branched alkyl group, a substituted or unsubstituted C3-C20 cycloalkyl group, a substituted or unsubstituted C2-C20 alkenyl group, a substituted or unsubstituted C2-C20 alkynyl group, and an aromatic group.

Preferably, in formula (I), $R_1$, $R_2$, and $R_3$ each independently represents any one or a combination of at least two selected from the group consisting of

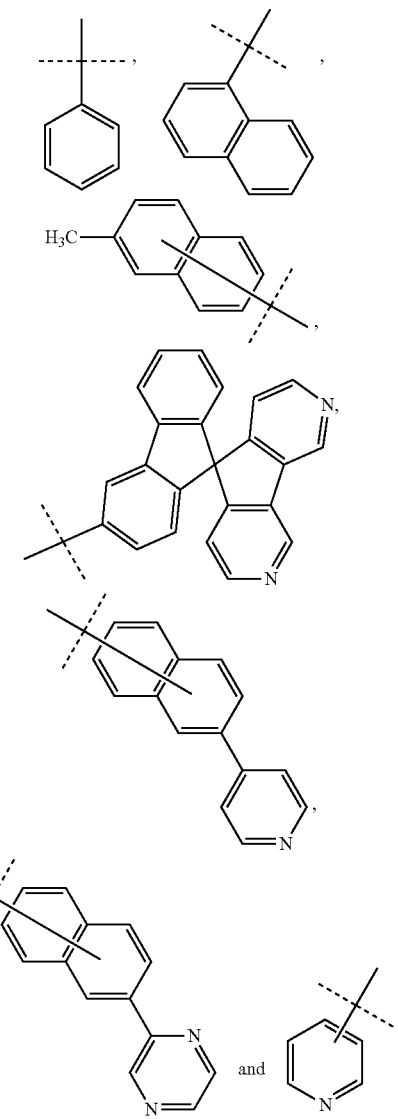

In a preferred specific embodiment, in formula (I), a, b and c are each independently selected from the group consisting of $CR_4$ and N; wherein $R_4$ is any one selected from the group consisting of a hydrogen atom, a deuterium atom, a halogen, a nitro group, a cyano group, a trifluoromethyl group, a C1-C8 linear alkyl group or branched alkyl group, a C6-C34 aryl group or a C2-C34 nitrogen-containing heterocyclic aryl.

In formula (I), $R_1$, $R_2$, and $R_3$ are each independently any one selected from the group consisting of a hydrogen atom, a deuterium atom, a halogen, a nitro group, a cyano group, a trifluoromethyl group, and the structure of $(R_5)_d\text{—}R_6\text{—}$, $$R_7-\overset{\overset{O}{\|}}{C}-\bigg|\ ,\quad R_8-\overset{\overset{O}{\|}}{\underset{\underset{O}{\|}}{S}}-\bigg|\ ,\quad \text{or}\quad R_9-\overset{\overset{O}{\|}}{\underset{R_{10}}{P}}-\bigg|\ .$$

In the structure of $(R_5)_d\text{—}R_6\text{—}$, $R_6$ is a C6-C34 aryl or a C2-C34 nitrogen containing heterocyclic aryl, $R_5$ is any one of a hydrogen atom, a deuterium atom, a halogen, a nitro group, a cyano group or a trifluoromethyl group, and d is an integer more than 1.

In the structure of $$R_7-\overset{\overset{O}{\|}}{C}-\bigg|\ ,$$

$R_7$ is any one of a C1-C4 alkyl, a C6-C12 aryl and a C6-C12 nitrogen containing heterocyclic aryl; or, in the structure of $$R_8-\overset{\overset{O}{\|}}{\underset{\underset{O}{\|}}{S}}-\bigg|\ ,$$

$R_8$ is a C1-C4 alkyl, a C6-C12 aryl and a C6-C12 nitrogen containing heterocyclic aryl; or, in the structure of $$R_9-\overset{\overset{O}{\|}}{\underset{R_{10}}{P}}-\bigg|\ ,$$

$R_9$ and $R_{10}$ are each independently selected from a C6-C12 aryl and a C6-C12 nitrogen containing heterocyclic aryl.

In a preferred specific embodiment, in formula (I), $R_1$, $R_2$, and $R_3$ are each independently any one or a combination of at least two selected from the group consisting of H—, D-, CN—, $CF_3$—, $NO_2$—, F—, Cl, Br—, and the like; and further preferably selected from the group consisting of -continued
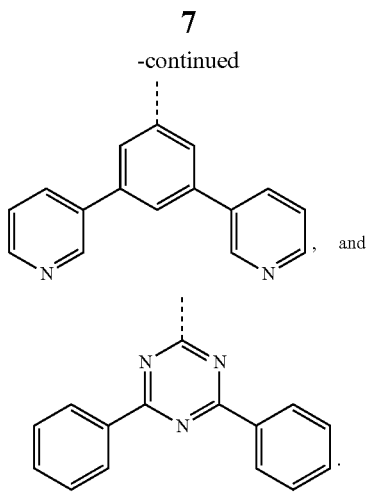
In a preferred specific embodiment, the electron transport material of the present disclosure comprises any one or a combination of at least two of
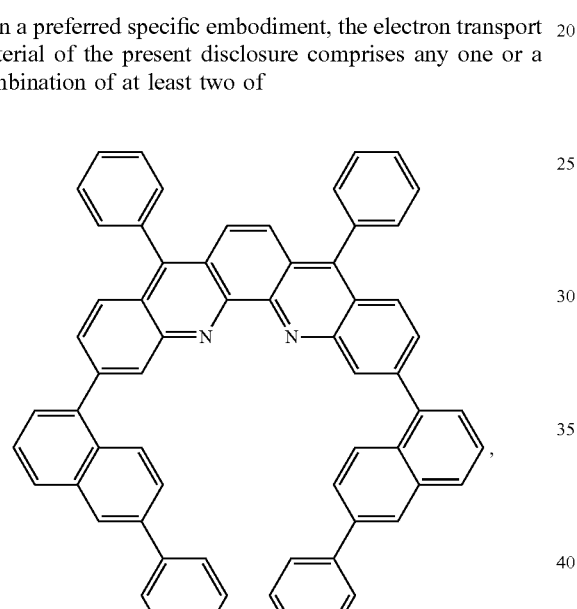
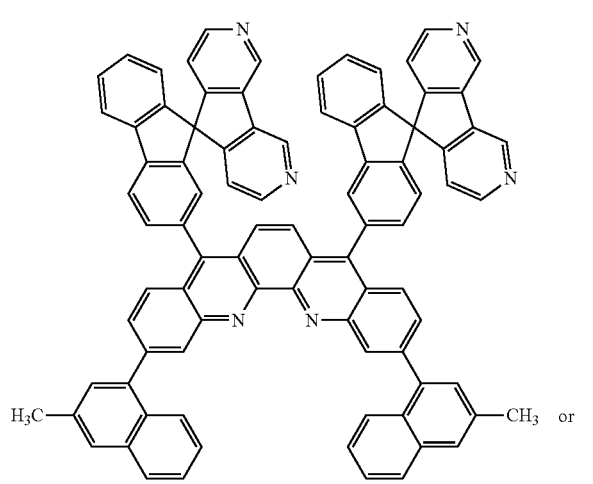
-continued
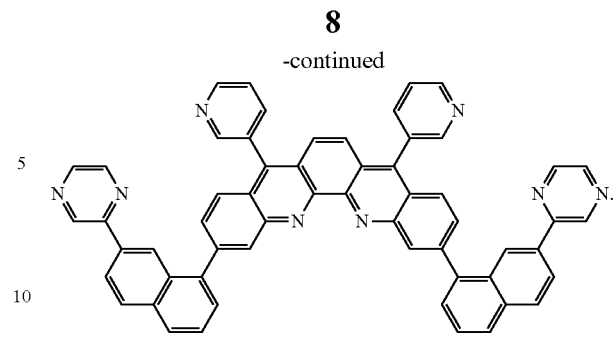
Illustratively, the electron transport material of the present disclosure comprises:
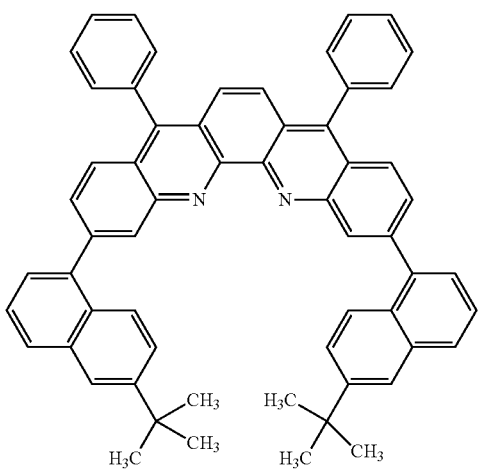
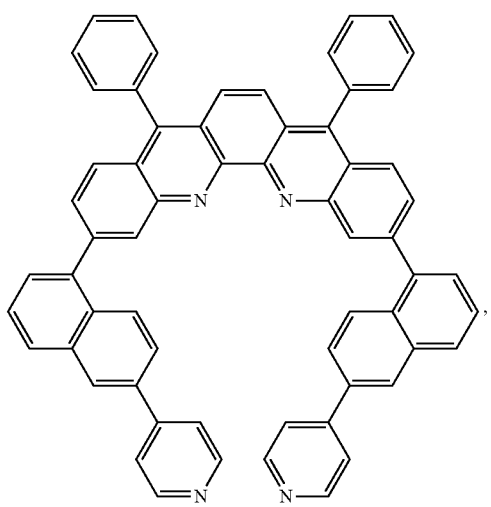

-continued
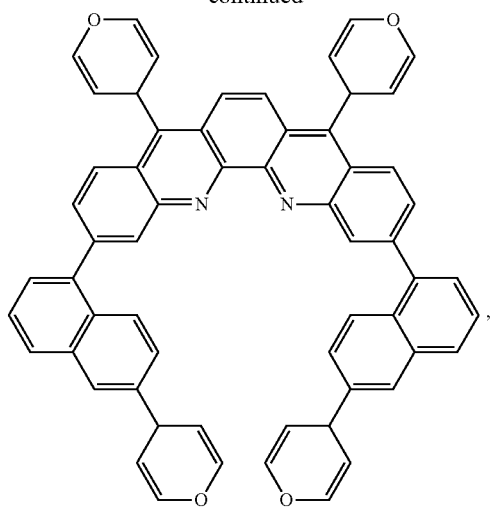
,
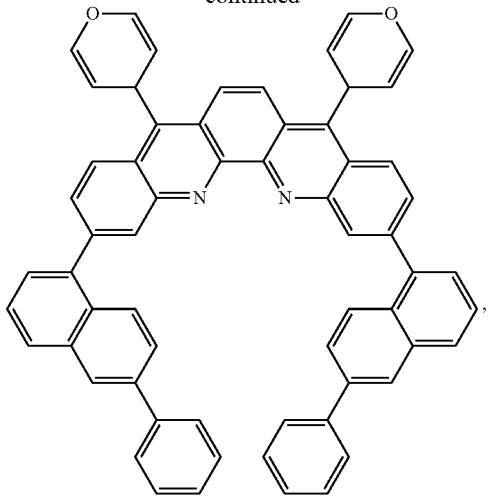
,
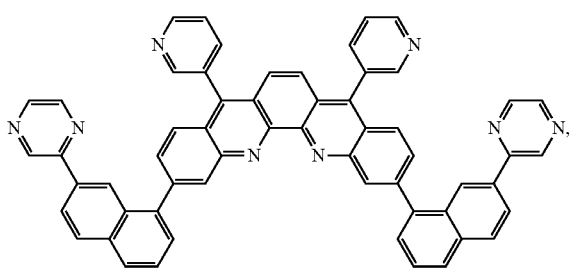
,
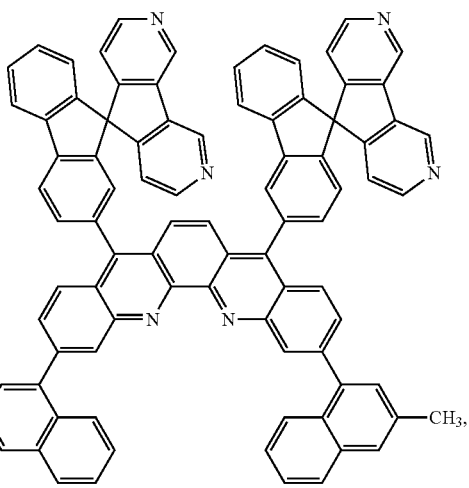
,
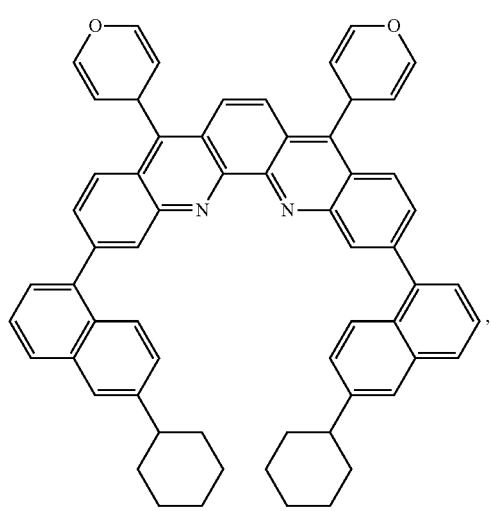
,
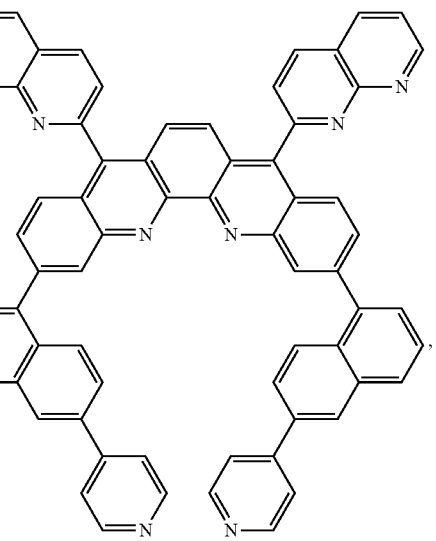
,

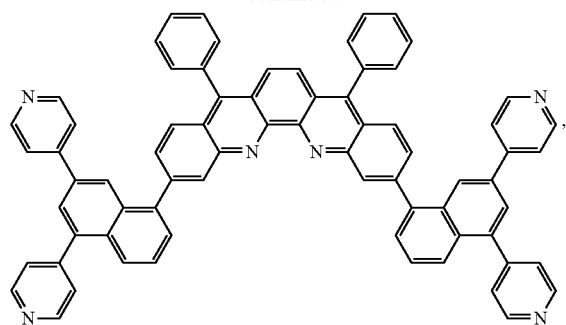
and the like.
The compounds having the structure represented by formula (I) provided by the present disclosure can be synthesized through the related technics, and the specific synthetic route includes the following steps:
Step (1):
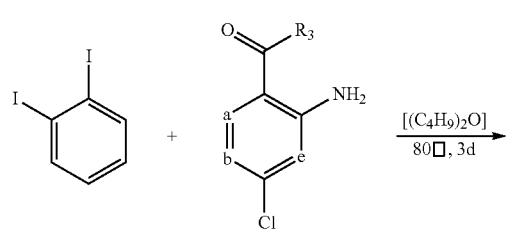
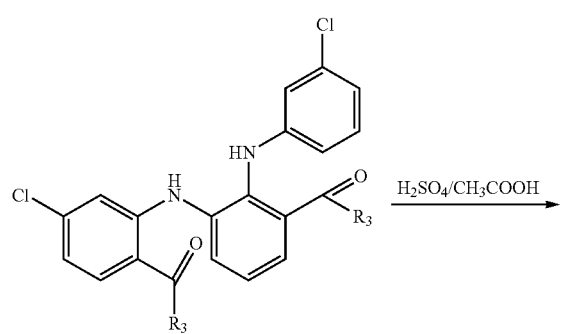
Step (2):
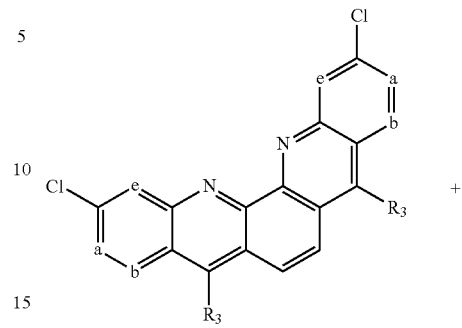
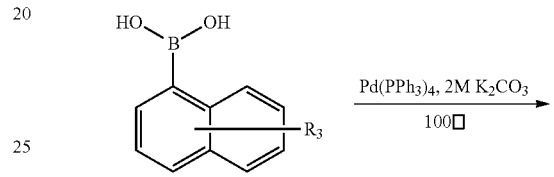
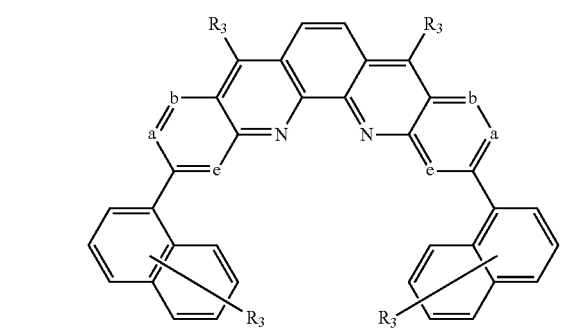
Exemplary preparation method, such as for
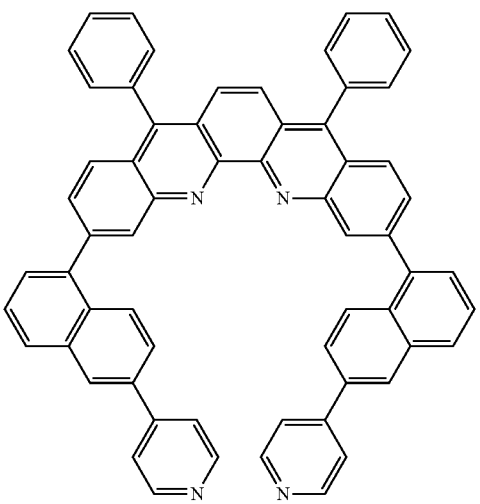 [SMILES: c1ccc(-c2c3ccc(-c4cccc5cc(-c6ccncc6)ccc45)cc3nc3c2ccc2c(-c4ccccc4)c4ccc(-c5cccc6cc(-c7ccncc7)ccc56)cc4nc23)cc1]

includes the following steps:

Step 1: Synthesis of intermediate a

Step 2:

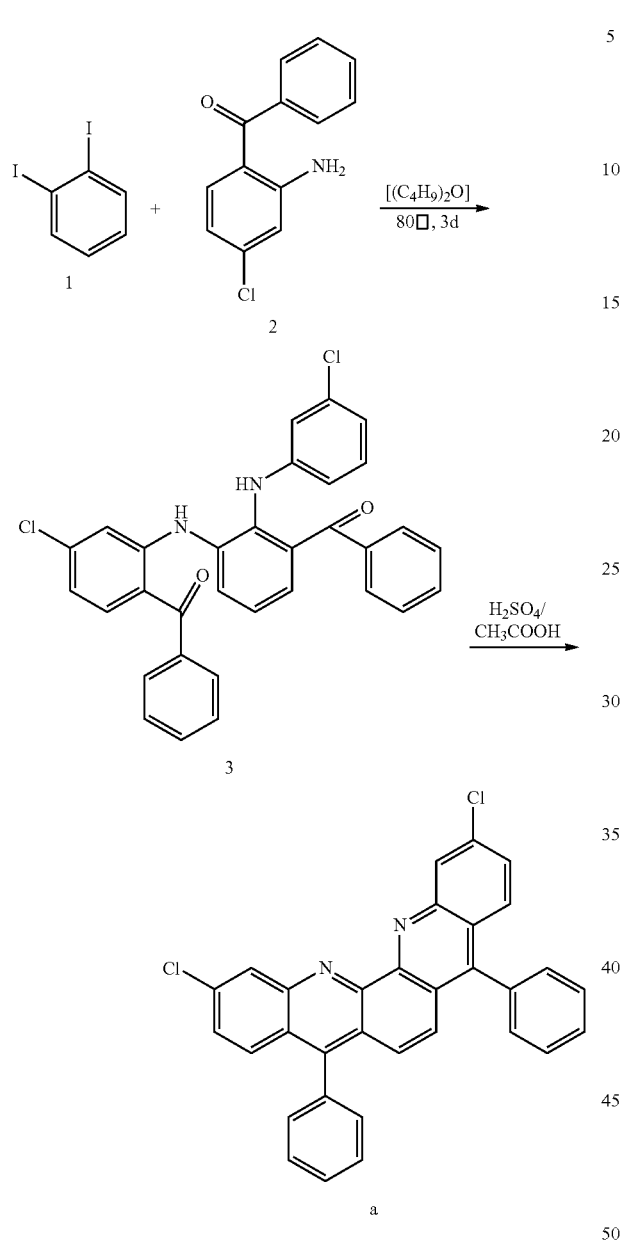

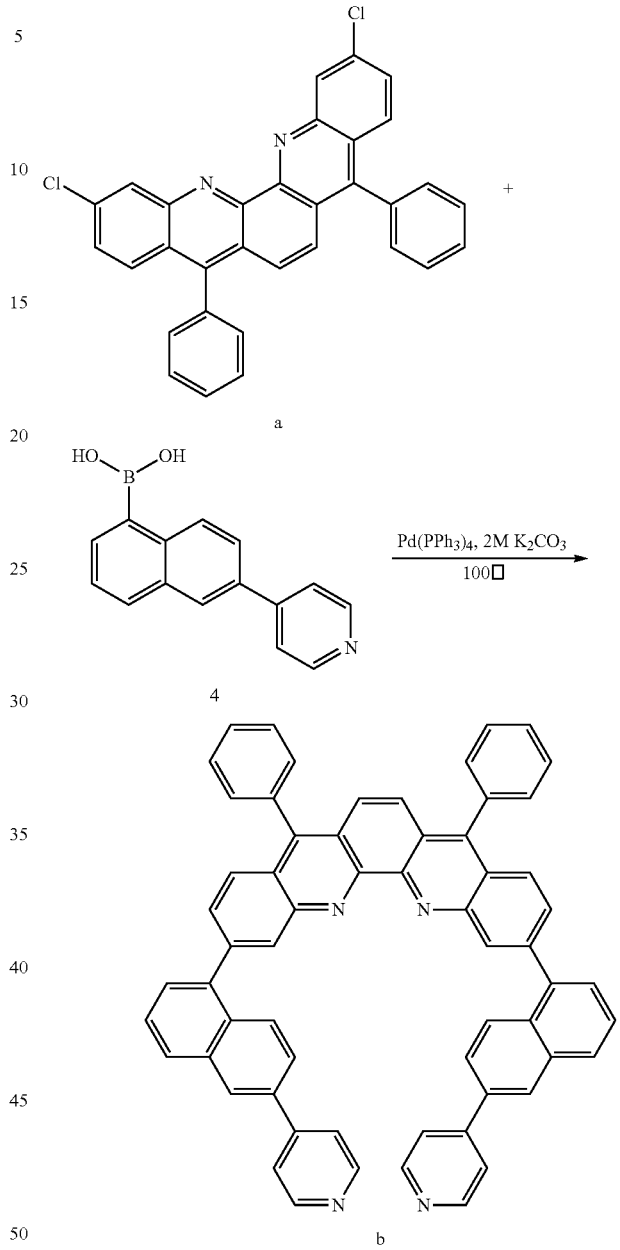

100 mL of n-butyl methyl ether is charged into a three-necked flask, and 1 mol of 1,2-diiodobenzene (raw material 1) and 2.2 mol of intermediate 2 are added thereto respectively under stirring to react therewith for 3 days at 80° C., and the solvent is removed by distillation under reduced pressure to give intermediate 3. Then, 30 mL of acetic acid is added to the three-necked flask, followed by the addition of 3 drops of concentrated sulfuric acid (98%) to react at 100° C. for 20 minutes. After the completion of reaction, the mixture is diluted with water and extracted with dichloromethane, the organic phase is washed with water and then dried over anhydrous sodium sulfate, the dichloromethane is removed by distillation to obtain the intermediate a (yield: 50%).

The intermediate a (1 mol) and intermediate 4 (2.2 mol) are dissolved in 100 mL of a solution of toluene in ethanol (a ratio of 5:1 by volume), followed by the addition of tetrakis (triphenylphosphine)palladium (1 mmol), and a solvent of 1% KOH (20 mL), then the reaction system is vacuumized and filled with nitrogen, and heated to reflux for 20 hours. After cooling, the solvent is removed by distillation under reduced pressure and the obtained product is extracted with dichloromethane. The organic phase is washed with water and then dried over anhydrous sodium sulfate, the dichloromethane is distilled off The crude product is eluted with a mobile phase of $CH_2Cl_2$ and ethyl acetate in a gradient elution to obtain the target product b (yield: about 83%).

Exemplary preparation method, such as for molecule
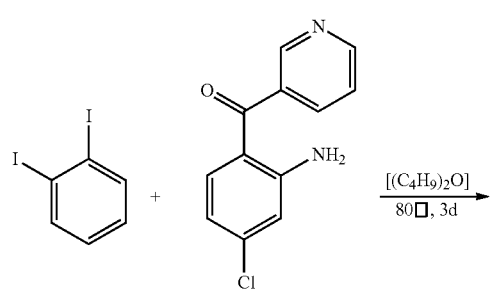
includes the following steps:
Step 1:
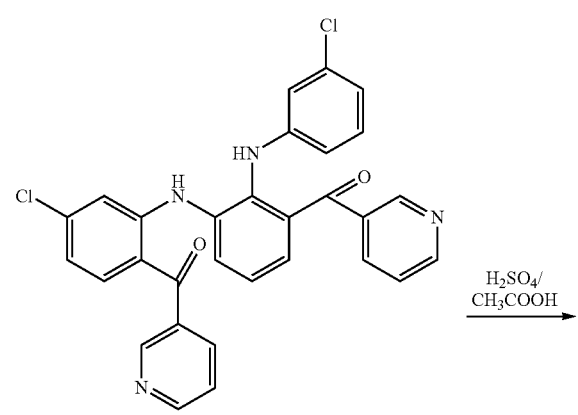
Step 2:
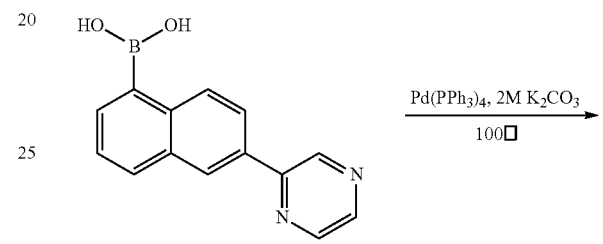
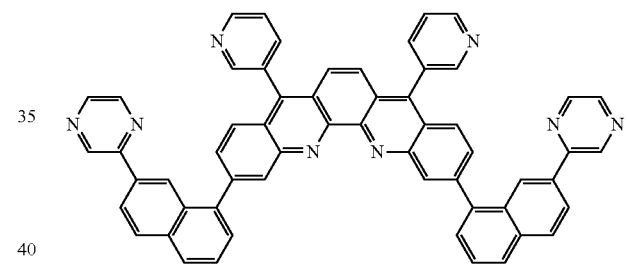
The yield of the above synthesis is about 80%.
Exemplary preparation method, such as for
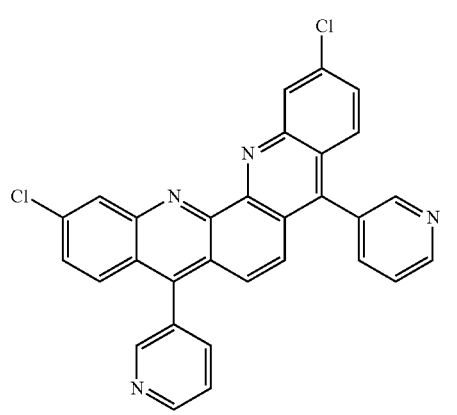
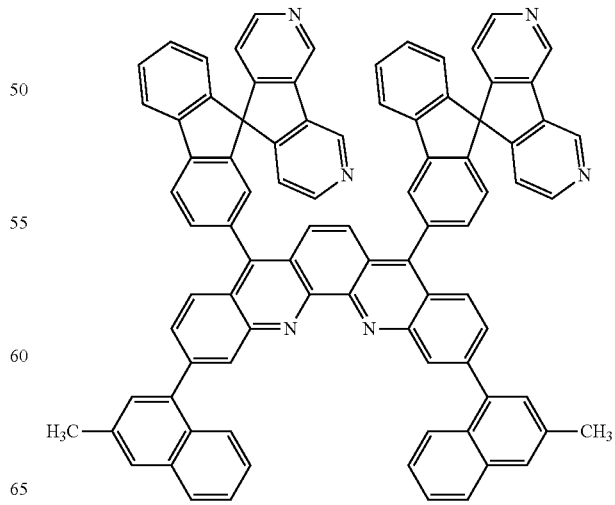

includes the following steps:
Step 1:
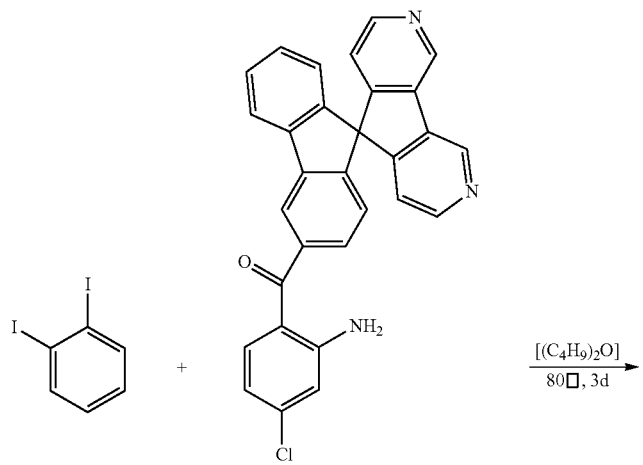
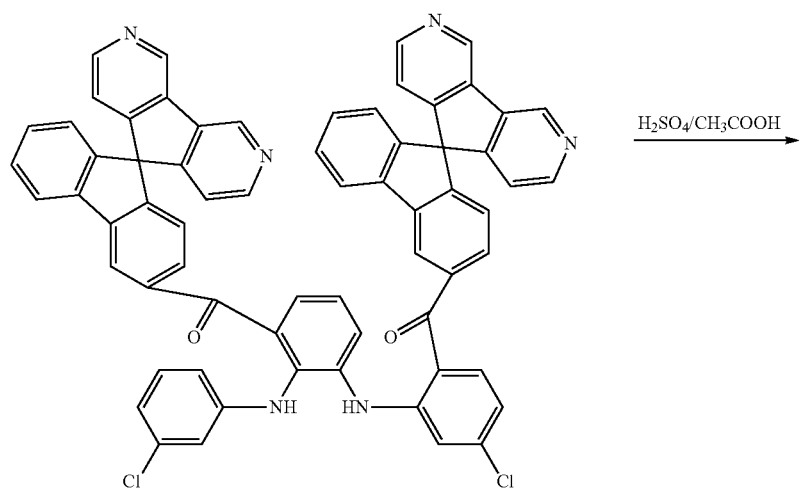
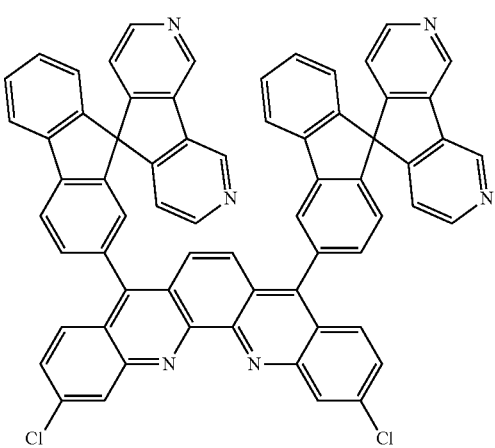

Step 2:

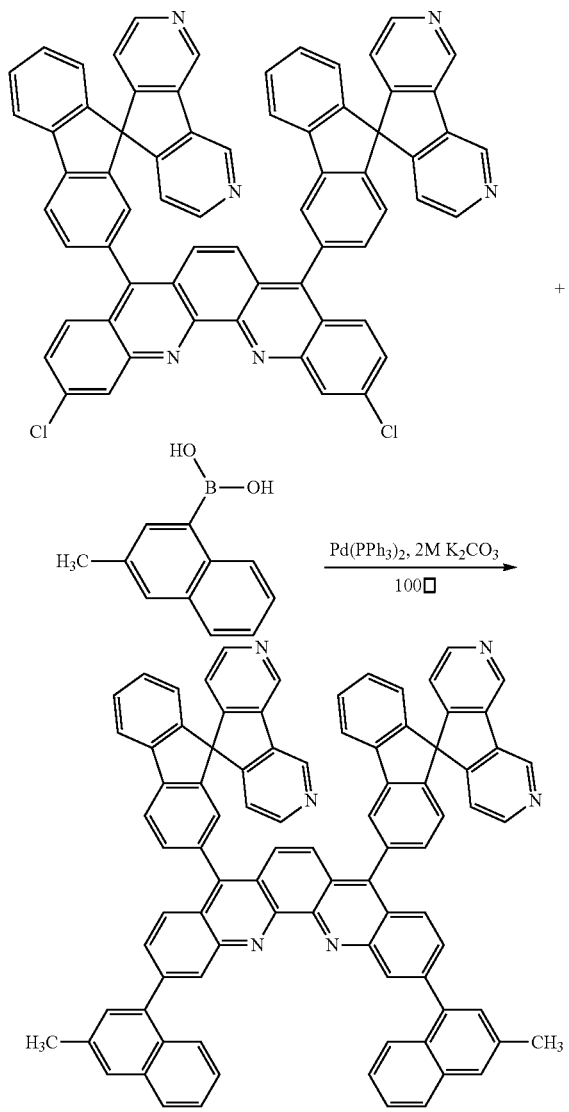

The yield of the above synthesis is about 70%.

In a specific embodiment, the present disclosure also provides an OLED display panel comprising a first electrode and a second electrode, wherein a laminate comprising a light emitting layer and an electron transport layer is disposed between the first electrode and the second electrode, and the material of the electron transport layer includes the electron transport material as previously described.

The OLED display panel exemplarily has a structure as shown in FIG. 1, which comprises a substrate 101, a first electrode 102 disposed on the substrate 101, a light emitting layer 103 and an electron transport layer 104 sequentially laminated on the first electrode 102, and a second electrode 105 formed thereon.

The electron transport layer 104 has a compound with a structure represented by formula (I).

In a specific embodiment, the laminate further comprises an electron injection layer, the material of the electron injection layer includes the electron transport material as previously described and a doped metal.

Figure 2:
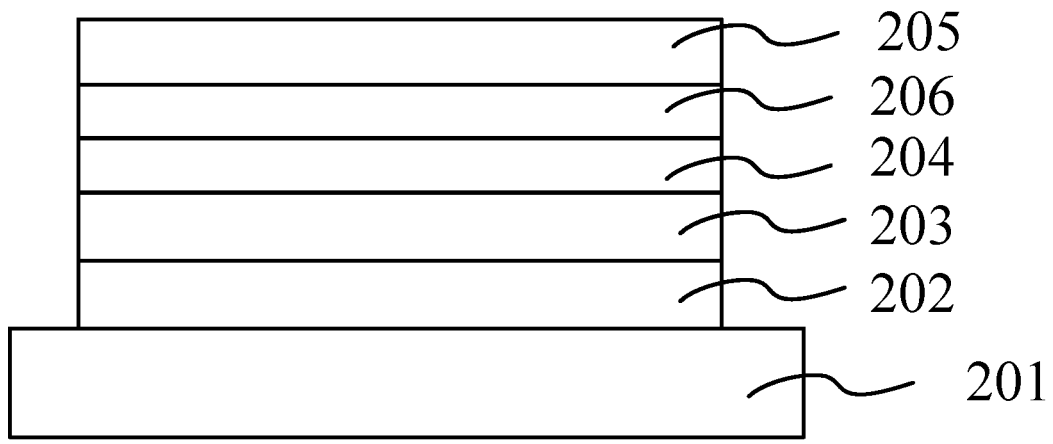
FIG. 2 is a cross-sectional structural representation of another OLED display panel provided in a specific embodiment of the present disclosure.

The OLED display panel exemplarily has a structure as shown in FIG. 2, which comprises a substrate 201, a first electrode 202 disposed on the substrate 201, a light emitting layer 203, an electron transport layer 204 and an electron injection layer 206 sequentially laminated on the first electrode 202, and a second electrode 205 formed thereon.

The electron transport layer 204 has a compound having a structure represented by formula (I), and the electron injection layer 206 includes a compound with a structure represented by formula (I) and a doped metal.

Preferably, the doped metal includes any one or a combination of at least two of sodium, potassium, calcium, cesium and ytterbium, such as a combination of sodium and potassium, a combination of calcium and sodium, a combination of potassium, calcium and ytterbium, a combination of calcium, cesium and ytterbium, and a combination of sodium, potassium and cesium, and the like.

Preferably, in the electron injection material, the content of the doped metal is 1-5 wt %, for example 1.2 wt %, 1.5 wt %, 1.7 wt %, 1.9 wt %, 2.1 wt %, 2.3 wt %, 2.5 wt %, 2.7 wt %, 3.0 wt %, 3.3 wt %, 3.5 wt %, 3.7 wt %, 3.9 wt %, 4.2 wt %, 4.6 wt %, and 4.8 wt %, and the like.

In a specific embodiment, the laminate further comprises any one or a combination of at least two of a hole injection layer and a hole transport layer.

In a specific embodiment, the OLED display panel comprises from bottom to top a first electrode, a hole injection layer, a hole transport layer, a light emitting layer, an electron transport layer, an electron injection layer, and a second electrode in sequence.

Figure 3:
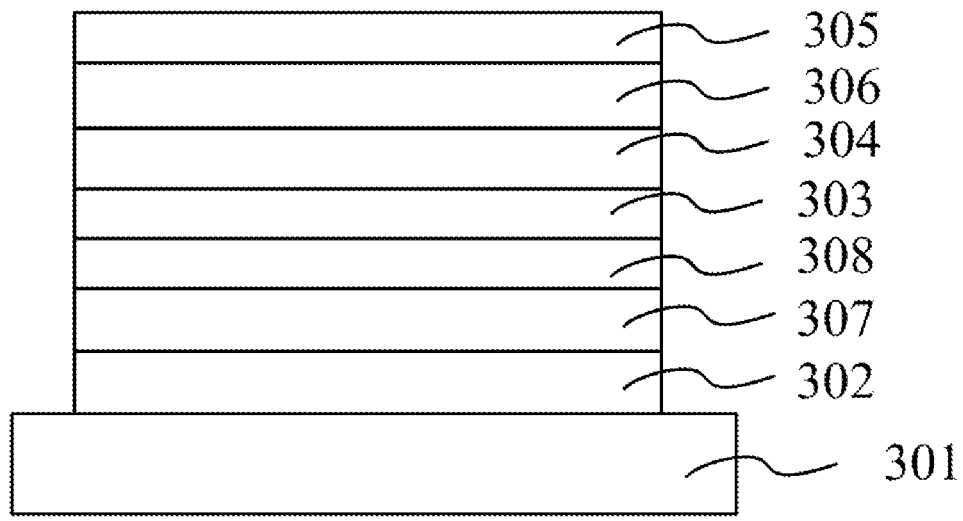
FIG. 3 is a cross-sectional structural representation of still another OLED display panel provided in a specific embodiment of the present disclosure.

The OLED display panel exemplarily has a structure as shown in FIG. 3, which comprises a substrate 301, a first electrode 302 disposed on the substrate 301, a hole injection layer 307, a hole transport layer 308, a light emitting layer 303, an electron transport layer 304 and an electron injection layer 306 sequentially laminated on the first electrode 302, and a second electrode 305 formed thereon.

The electron transport layer 304 has a compound with a structure represented by formula (I), and the electron injection layer 306 includes a compound with a structure represented by formula (I) and a doped metal.

The material of the hole injection layer exemplarily includes molybdenum oxide, vanadium oxide, ruthenium oxide, tungsten oxide and manganese oxide, and the like, and may further include phthalocyanine-based compounds such as phthalocyanine, copper phthalocyanine, and the like, and may also include a polymer material such as poly (ethylene dioxythiophene)/poly(styrene sulfonic acid) and the like.

The material of the hole transport layer may exemplarily be an aromatic amine-based materials such as aromatic amine compounds of 4,4'-bis[N-(3-methylphenyl)-N-aniline]biphenyl, NPB (4,4'-bis[N-(1-naphthyl)-N-aniline]biphenyl), and the like.

Preferably, the first electrode is an anode and the second electrode is a cathode.

In a specific embodiment, the first electrode at least comprises a reflective film and a conductive transparent thin film.

In a specific embodiment, the reflective film includes silver.

The conductive transparent thin film is selected from an ITO (indium tin oxide) film and/or an IZO (indium zinc oxide) film.

In a specific embodiment, the second electrode is selected from any one of magnesium silver alloy, silver metal, silver ytterbium alloy and silver rare-earth metal alloy.

Figure 4:
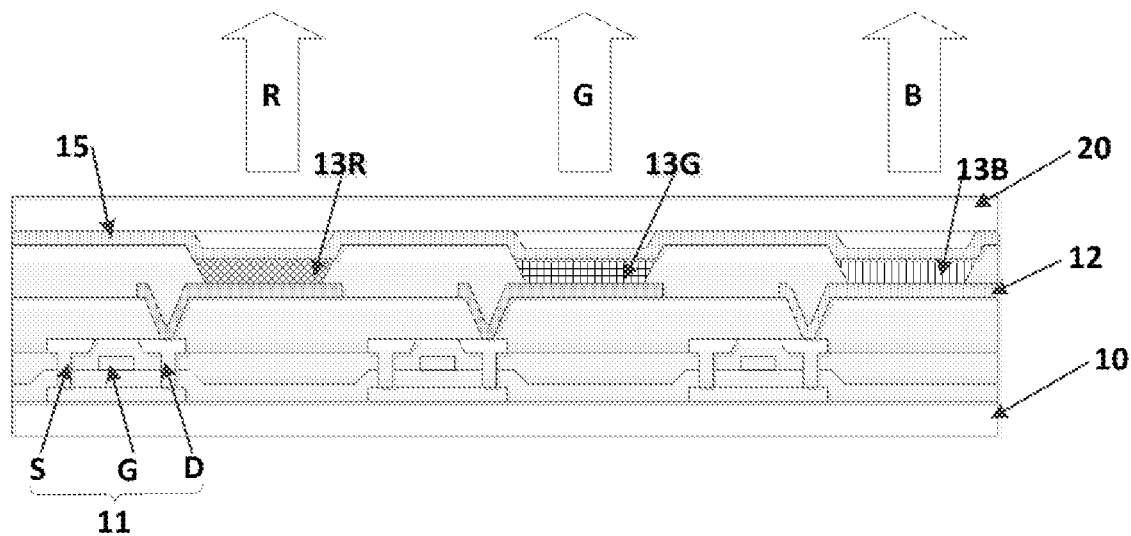
FIG. 4 is a cross-sectional structural representation of still another OLED display panel provided in a specific embodiment of the present disclosure.

In a further specific embodiment, the OLED display panel of the present disclosure exemplarily has a structure as shown in FIG. 4, which comprises a lower substrate 10 and an upper substrate (or a package film layer) 20, an array of TFT (thin film transistor) 11, an anode 12, a light emitting layer 13R corresponding to the R pixel region, a light emitting layer 13G corresponding to the G pixel region, a light emitting layer 13B corresponding to the B pixel region, and a cathode 15 on the lower substrate 10. In a specific embodiment, the present disclosure also provides an electronic device comprising the OLED display panel as previously described.

EXAMPLES

Example 1

An OLED display panel, the structure of the device is as follows: a substrate 301, a first electrode 302 (ITO electrode), a hole injection layer F4-TCNQ

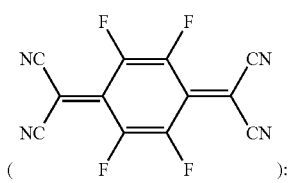 [SMILES: N#CC(C#N)=c1c(F)c(F)c(=C(C#N)C#N)c(F)c1F]

NPB

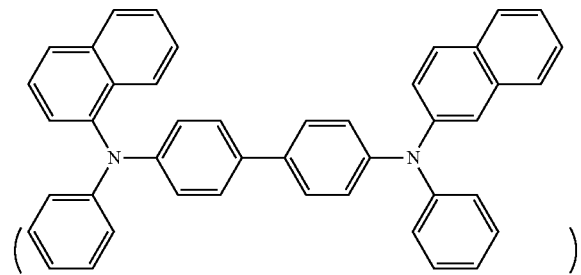

(1%, 10 nm), a hole transport layer TAPC

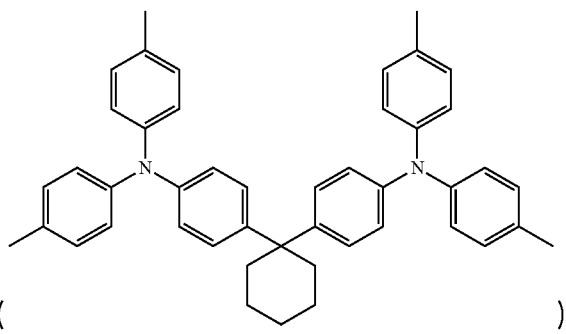

(125 nm), a light emitting layer DPVBi

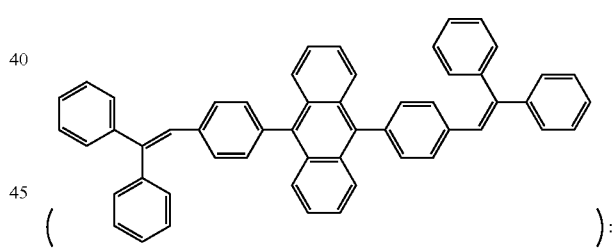

BCzVBi

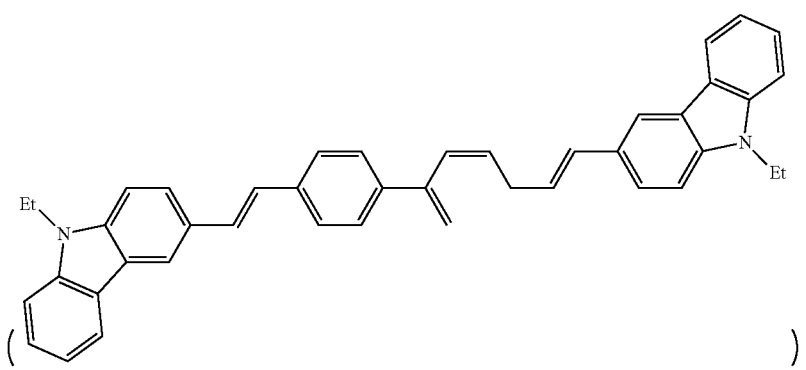

(5%, 25 nm), an electron transport layer 10 nm, an electron injection layer 34 nm, and a cathode Ag (15 nm) sequentially laminated on the substrate 301.

The electron transport layer 304 is

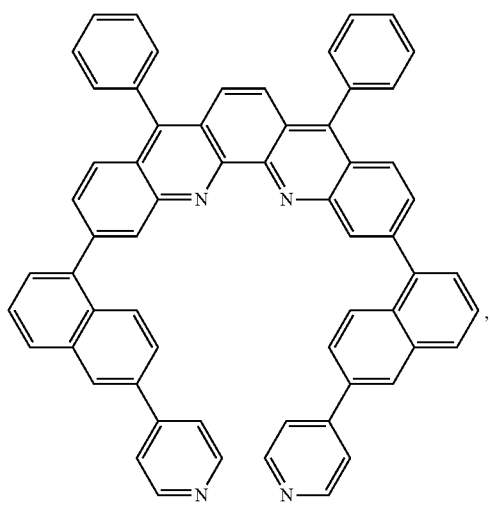 [SMILES: c1ccc(-c2c3ccc(-c4cccc5cc(-c6ccncc6)ccc45)cc3nc3c2ccc2c(-c4ccccc4)c4ccc(-c5cccc6cc(-c7ccncc7)ccc56)cc4nc23)cc1]

, and the electron injection layer 306 includes

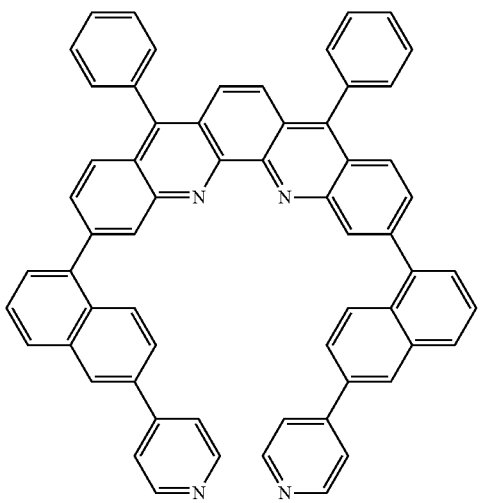 [SMILES: c1ccc(-c2c3ccc(-c4cccc5cc(-c6ccncc6)ccc45)cc3nc3c2ccc2c(-c4ccccc4)c4ccc(-c5cccc6cc(-c7ccncc7)ccc56)cc4nc23)cc1]

doped with 1% of Yb.

Example 2

An OLED display panel, the structure of the device is as follows: a substrate 301, a first electrode 302 (ITO electrode), a hole injection layer F4-TCNQ

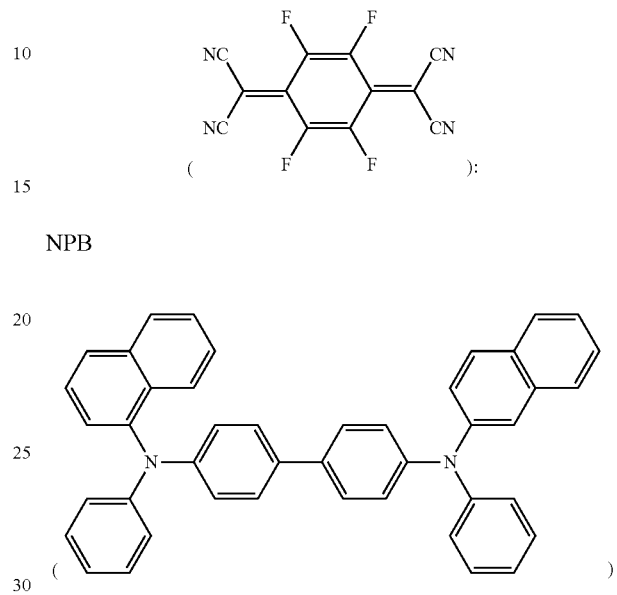

( ):

NPB ( )

(1%, 10 nm), a hole transport layer TAPC

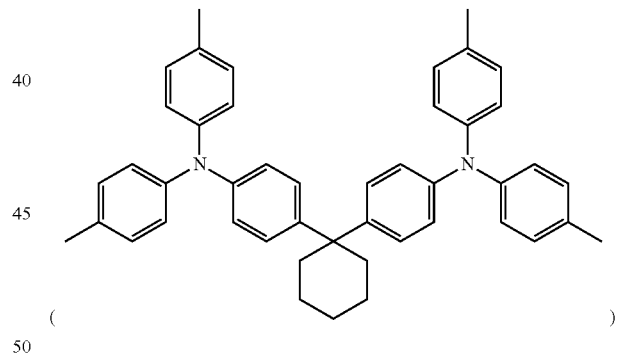

( )

(125 nm), a light emitting layer DPVBi

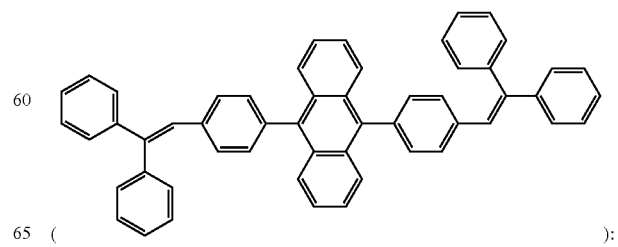

( ):

BCzVBi

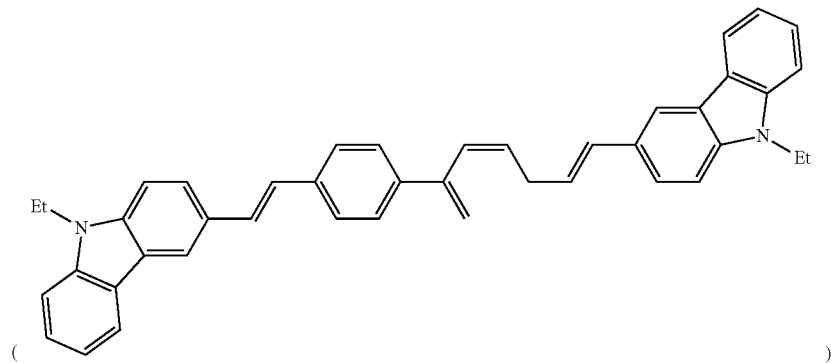 [SMILES: C=C(/C=C\C/C=C/c1ccc2c(c1)c1ccccc1n2CC)c1ccc(/C=C/c2ccc3c(c2)c2ccccc2n3CC)cc1]

(5%, 25 nm), an electron transport layer 10 nm, an electron injection layer 34 nm, and a cathode Ag (15 nm) sequentially laminated on the substrate 301.

The electron transport layer 304 is

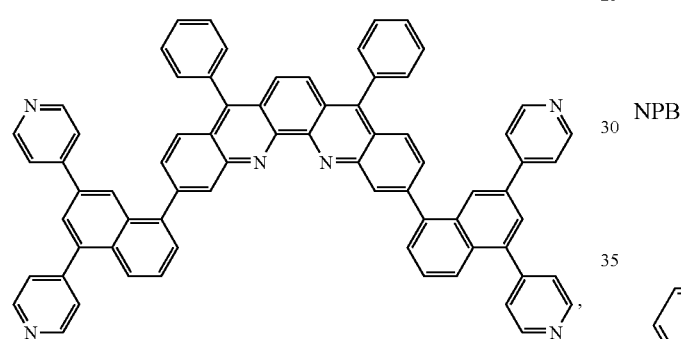

and the electron injection layer 306 includes

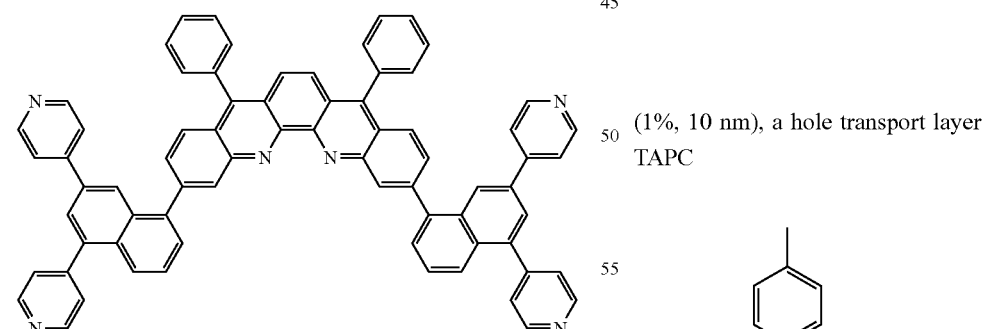

doped with 1% of Yb.

Comparative Example 1

An OLED display panel, the structure of the device is as follows: a substrate 301, a first electrode 302 (ITO electrode), a hole injection layer F4-TCNQ

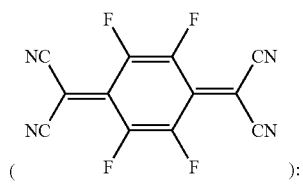 [SMILES: N#CC(C#N)=c1c(F)c(F)c(=C(C#N)C#N)c(F)c1F]

NPB

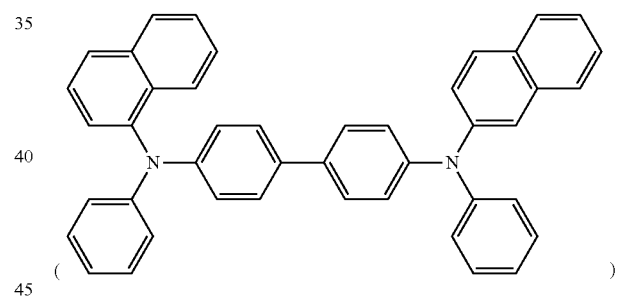

(1%, 10 nm), a hole transport layer TAPC

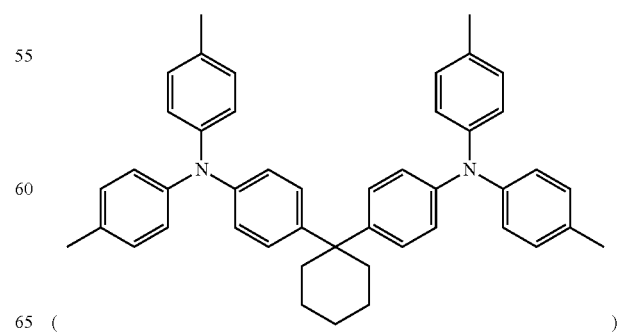

(125 nm), a light emitting layer DPVBi

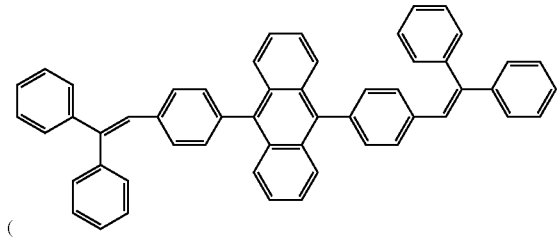

):

BCzVBi

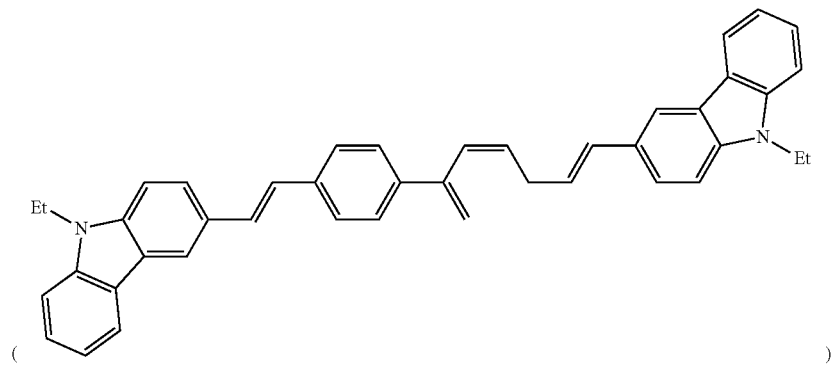 [SMILES: C=C(/C=C\C/C=C/c1ccc2c(c1)c1ccccc1n2CC)c1ccc(/C=C/c2ccc3c(c2)c2ccccc2n3CC)cc1]

(

)

(5%, 25 nm), an electron transport layer 10 nm, an electron injection layer 34 nm, and a cathode Ag (15 nm) sequentially laminated on the substrate 301.

The electron transport layer 304 is

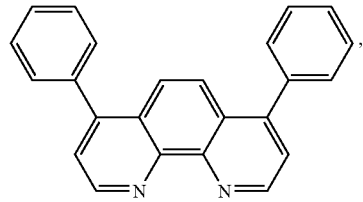 [SMILES: c1ccc(-c2ccnc3c2ccc2c(-c4ccccc4)ccnc23)cc1]

, and the electron injection layer 306 includes

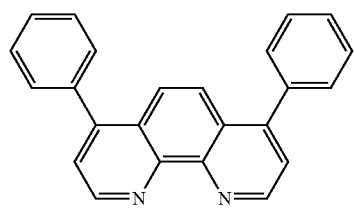 [SMILES: c1ccc(-c2ccnc3c2ccc2c(-c4ccccc4)ccnc23)cc1]

doped with 1% of Yb.

Example 3

An OLED display panel, the structure of the device is as follows: a substrate 301, a first electrode 302 (ITO electrode), a hole injection layer F4-TCNQ

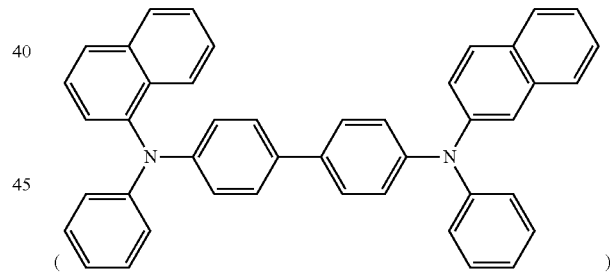

):

NPB

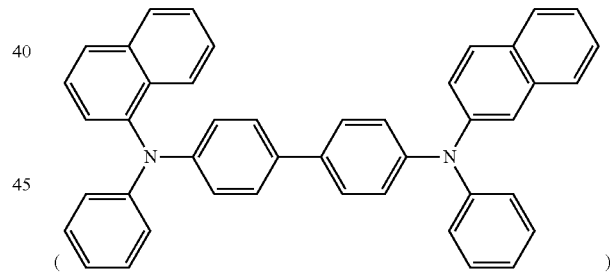

(1%, 10 nm), a hole transport layer TAPC

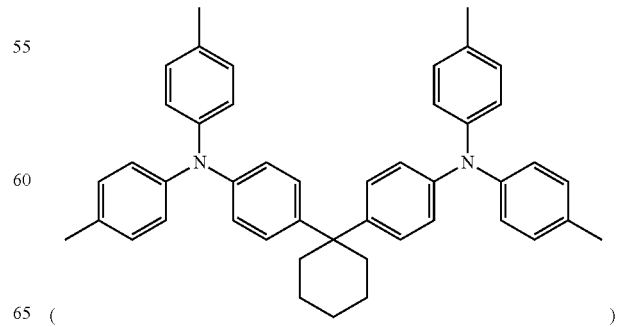

(

)

(125 nm), a light emitting layer DPVBi

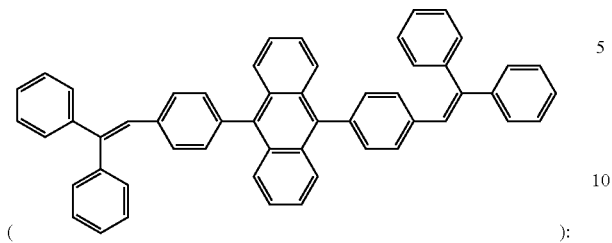

(  ):

BCzVBi

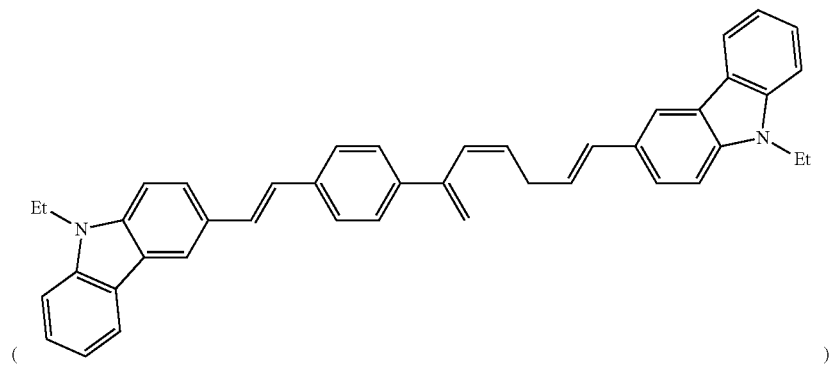 [SMILES: C=C(/C=C\C/C=C/c1ccc2c(c1)c1ccccc1n2CC)c1ccc(/C=C/c2ccc3c(c2)c2ccccc2n3CC)cc1]

(  )

(5%, 25 nm), an electron transport layer 10 nm, an electron injection layer 34 nm, and a cathode Ag (15 nm) sequentially laminated on the substrate 301.

The electron transport layer 304 is

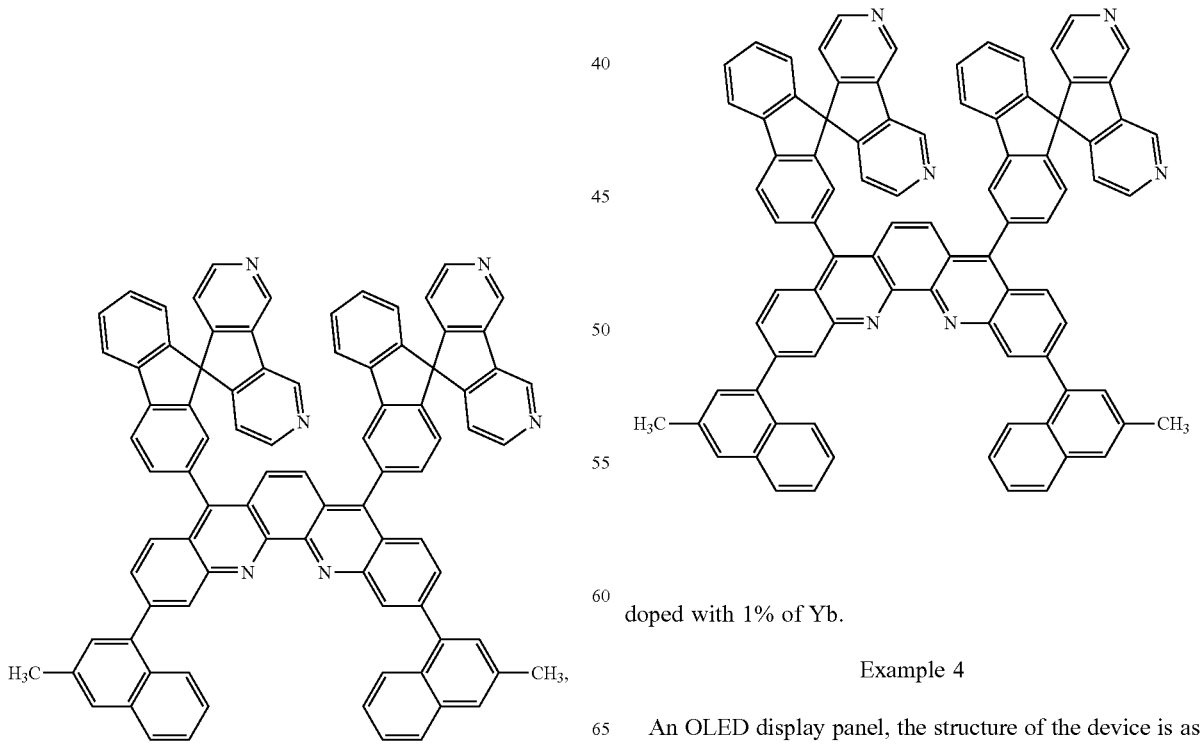

and the electron injection layer 306 includes doped with 1% of Yb.

Example 4

An OLED display panel, the structure of the device is as follows: a substrate 301, a first electrode 302 (ITO electrode), a hole injection layer F4-TCNQ (125 nm), a light emitting layer DPVBi
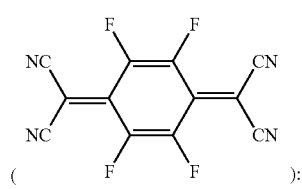 [SMILES: N#CC(C#N)=c1c(F)c(F)c(=C(C#N)C#N)c(F)c1F]
NPB
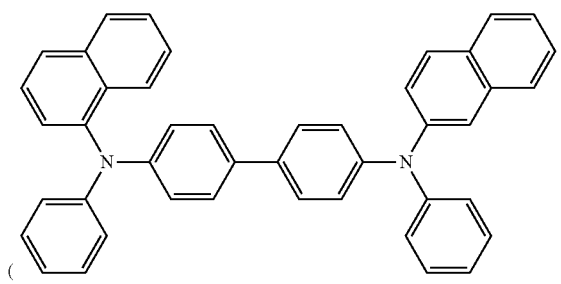
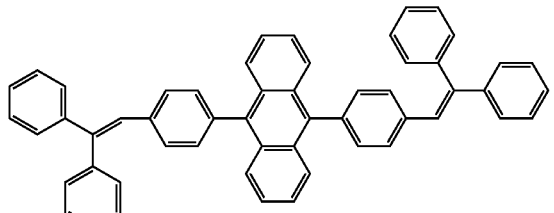
BCzVBi
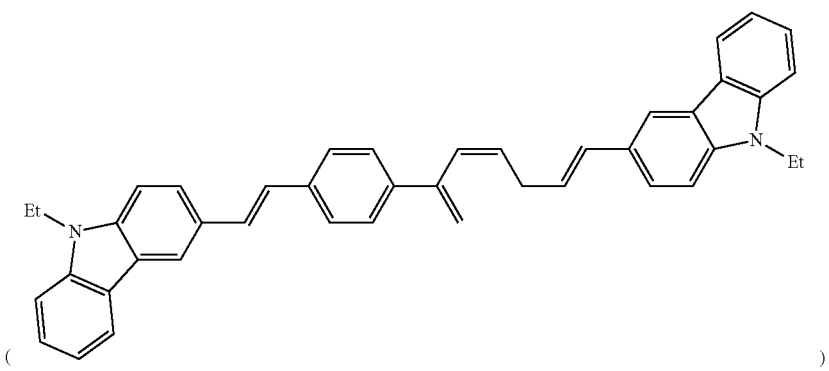 [SMILES: C=C(/C=C\C/C=C/c1ccc2c(c1)c1ccccc1n2CC)c1ccc(/C=C/c2ccc3c(c2)c2ccccc2n3CC)cc1]
(1%, 10 nm), a hole transport layer TAPC
(5%, 25 nm), an electron transport layer 10 nm, an electron injection layer 34 nm, and a cathode Ag (15 nm) sequentially laminated on the substrate 301.
The electron transport layer 304 is
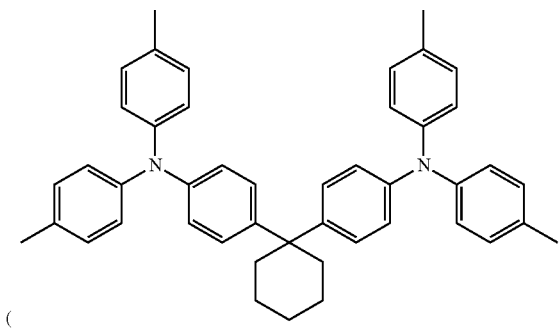
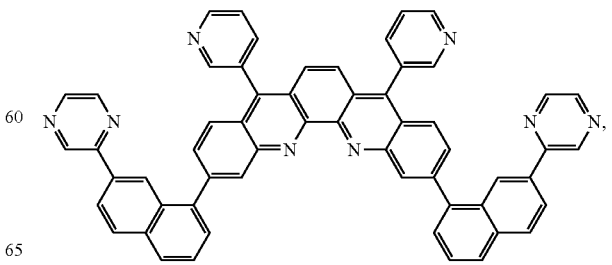

and the electron injection layer 306 includes

[chemical structure]

doped with 1% of Yb.

Example 5

An OLED display panel, the structure of the device is as follows: a substrate 301, a first electrode 302 (ITO electrode), a hole injection layer F4-TCNQ

[chemical structure]

NPB

[chemical structure]

(1%, 10 nm), a hole transport layer TAPC

[chemical structure]

(125 nm), a light emitting layer Ir(ppy)$_3$

[chemical structure]

mCP

[chemical structure]

(6%, 35 nm), an electron transport layer 10 nm, an electron injection layer 34 nm, and a cathode Ag (15 nm) sequentially laminated on the substrate 301.

The electron transport layer 304 is

[chemical structure]

and the electron injection layer 306 includes molecule

[chemical structure]

doped with 1% of Yb.

Performance Test

The OLED display panels provided in the Examples and the Comparative Example were subjected to the following performance tests:

Tg was measured using the differential scanning calorimetry, and the external quantum efficiency and voltage of the device were detected using a voltmeter such as the Spectroscan PR 705 spectrometer or Keithley 236 current & voltage source measurement system, and the voltage and external quantum efficiency were determined under a current density of 10 mA/cm².

The test results were as shown in Table 1.

TABLE 1

| Examples | Voltage, V | Tg, ° C. | Efficiency, EQE |
|---|---|---|---|
| Example 1 | 3.3 | 110 | 6.2% |
| Comparative Example 1 | 4 | 62 | 5% |
| Example 2 | 3.2 | 110 | 7.3% |
| Example 3 | 3.2 | 112 | 7% |
| Example 4 | 3.4 | 150 | 6.5% |
| Example 5 | 3.7 | 110 | 30% |

Applicant has stated that although the detailed process equipment and process flow of the present disclosure have been described by the above examples in the present disclosure, the present disclosure is not limited thereto, that is to say, it is not meant that the present disclosure has to be implemented depending on the above detailed process equipment and process flow. It will be apparent to those skilled in the art that any improvements made to the present disclosure, equivalent replacements to the raw materials of the products of the present disclosure and addition of adjuvant ingredients, and choices of the specific implementations, etc., all fall within the protection scope and the disclosure scope of the present disclosure.

What is claimed is:

1. An electron transport material comprising any one of the structures of

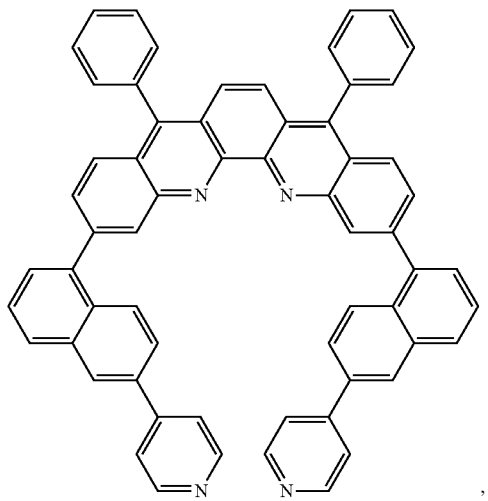

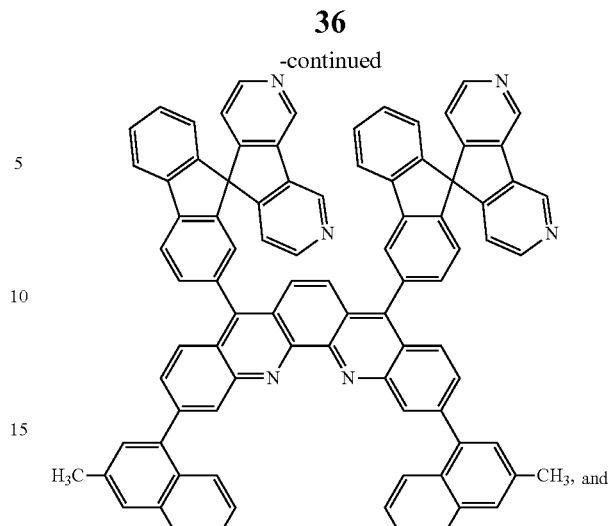

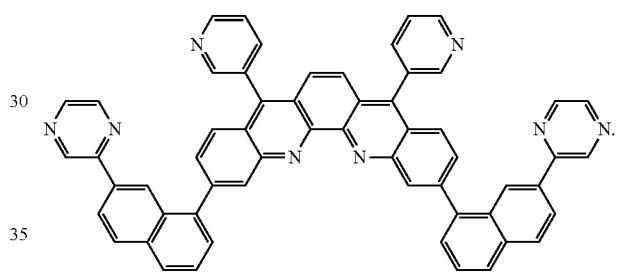

2. An OLED display panel comprising a first electrode and a second electrode, wherein a laminate comprising a light emitting layer and an electron transport layer is disposed between the first electrode and the second electrode, and wherein a material of the electron transport layer comprises any one of the structures of

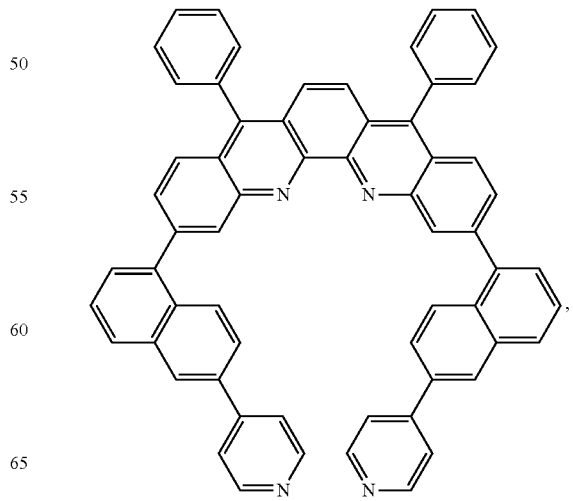

-continued

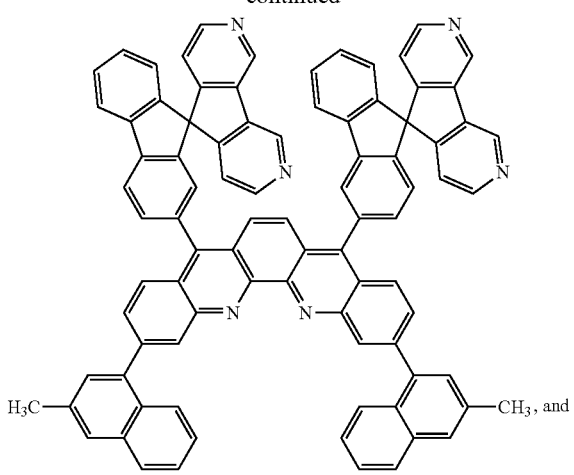

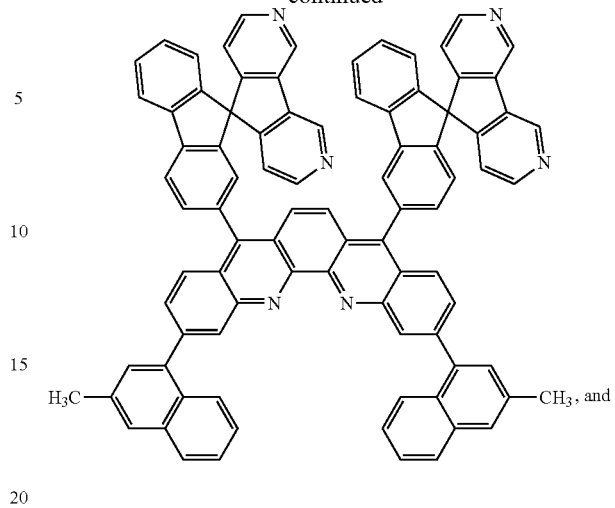

3. The OLED display panel of claim 2, wherein the laminate further comprises an electron injection layer, wherein a material of the electron injection layer includes an electron transport material and a metal dopant, wherein the electron transport material comprises any one of the structures of

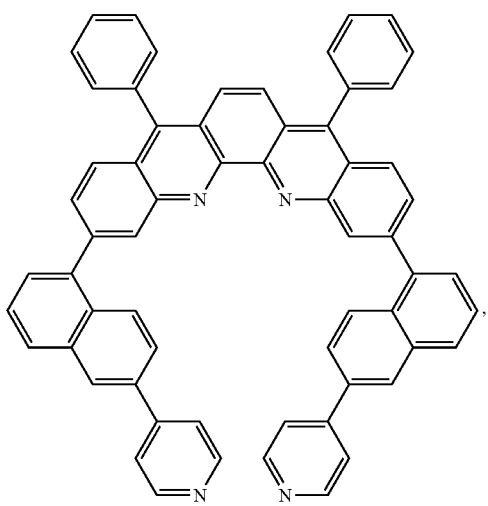

4. The OLED display panel of claim 3, wherein the metal includes any one or a combination of at least two of sodium, potassium, calcium, cesium and ytterbium.

5. The OLED display panel of claim 3, wherein the concentration of the metal is 1-5 wt % in the electron injection material.

6. The OLED display panel of claim 2, wherein the laminate further comprises a hole injection layer and a hole transport layer.

7. The OLED display panel of claim 6, wherein the first electrode, the hole injection layer, the hole transport layer, the light emitting layer, the electron transport layer, the electron injection layer, and the second electrode are displaced from bottom to top in sequence.

8. The OLED display panel of claim 2, wherein the first electrode is an anode and the second electrode is a cathode.

9. The OLED display panel of claim 2, wherein the first electrode comprises at least a reflective film and a conductive transparent thin film.

10. The OLED display panel of claim 9, wherein the reflective film comprises silver;

and wherein the conductive transparent thin film comprises an ITO film and an IZO film.

11. The OLED display panel of claim 2, wherein the second electrode is formed of any one of a magnesium silver alloy, silver metal, a silver ytterbium alloy, and a silver rare-earth metal alloy.

12. The OLED display panel of claim 2, comprising a first electrode and a second electrode, wherein a laminate comprising a light emitting layer and an electron transport layer is disposed between the first electrode and the second electrode, and a material of the electron transport layer includes an electron transport material comprises any one of the structures of

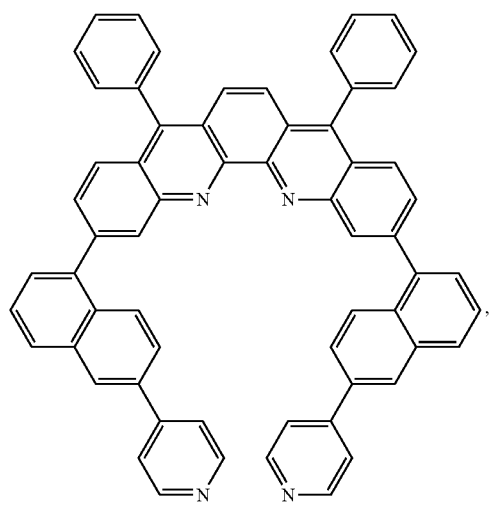

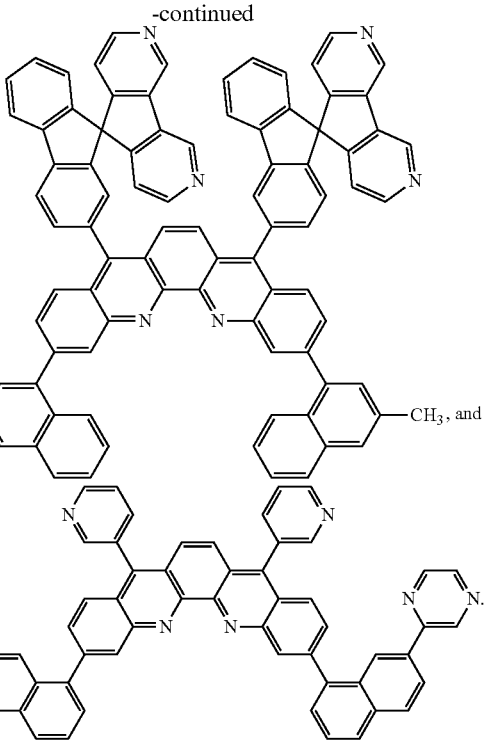

* * * * *